United States Patent [19]

Rappaport

[11] Patent Number: 5,126,439
[45] Date of Patent: Jun. 30, 1992

[54] ARTIFICIAL DNA BASE PAIR ANALOGUES

[75] Inventor: Harry P. Rappaport, Philadelphia, Pa.

[73] Assignee: Temple University, Philadelphia, Pa.

[21] Appl. No.: 247,560

[22] Filed: Sep. 22, 1988

Related U.S. Application Data

[63] Continuation-in-part of Ser. No. 99,744, Sep. 22, 1987, abandoned.

[51] Int. Cl.⁵ .............................................. C07H 21/00
[52] U.S. Cl. ..................................... 536/29; 536/27; 536/28; 536/55; 435/6
[58] Field of Search ............... 536/27, 28, 29, 55; 435/6

[56] References Cited

U.S. PATENT DOCUMENTS

| | | | |
|---|---|---|---|
| 3,843,629 | 10/1974 | Scheit et al. | 536/28 |
| 4,211,773 | 7/1980 | Lopez et al. | 514/49 |
| 4,468,384 | 8/1984 | Bardos et al. | 514/49 |

FOREIGN PATENT DOCUMENTS

| | | | |
|---|---|---|---|
| 8605518 | 9/1986 | World Int. Prop. O. | 435/6 |
| 8605519 | 9/1986 | World Int. Prop. O. | 435/6 |

OTHER PUBLICATIONS

Armato, Science News, 137:88-90, 94 (1990).
Kunkel et al., Mutation Research, vol. 94, pp. 413-419 (1982).
Dickerson et al., J. Med. Biol., vol. 149, pp. 761-786 (1981).
Nelson et al., Biopolymers, vol. 20, pp. 2509-2531 (1981).
Chu et al., Biopolymers, vol. 22, pp. 1235-1246 (1983).
Tibanyenda et al., Eur. J. Biochem., vol. 139, pp. 19-27 (1984).
Millican et al., Nucleic Acids Research, vol. 12, pp. 7435-7453 (1984).
Salisbury et al., J. Chem. Soc., Chem. Commun., pp. 985-986 (1985).
Brown et al., Nature, vol. 315, pp. 604-606 (1985).
Aboul-ela et al., Nucleic Acid Research, vol. 13, pp. 4811-4824 (1985).
Huynh-Dinh et al., Proc. Nat. Acad. Sci., USA, vol. 82, pp. 7510-7514 (1985).
Kneale et al., J. Mol. Biol., vol. 186 pp. 805-814 (1985).
Martin et al., Nucleic Acid Research, vol. 14, pp. 3773-3790 (1986).
Evan et al., Nucleic Acid Research, vol. 14, pp. 4267-4280 (1986).
Eritja et al., Nucleic Acid Research, vol. 14, pp. 5869-5884 (1986).
Hunter et al., J. Mol. Biol., vol. 190, pp. 605-618 (1986).
Charczuk et al. Nucleic Acid Research, vol. 14, pp. 9530-9531 (1986).
Goodman et al., J. Mol. Biol., vol. 88, pp. 423-435 (1974).
Fersht et al., Proc. Nat. Acad. Sci. USA, vol. 78, pp. 4251-4255 (1981).
Kunkel et al., J. Biol. Chem., vol. 256, pp. 9883-9889 (1981).
Fersht et al., J. Mol. Biol., vol. 165, pp. 655-667, (1983).
Fersht et al., J. Mol. Biol., vol. 165, pp. 669-682, (1983).
Lu et al., Proc. Nat. Acad. Sci USA, vol. 80, pp. 4639-4643 (1983).
Patten et al., Biochem., vol. 23, pp. 1613-1618 (1984).
Kramer et al., Cell, vol. 38, pp. 879-887 (1984).
Dohet et al., Proc. Nat. Acad. Sci. USA, vol. 82, pp. 503-505, (1985).
Hunter et al., Nature, vol. 320, pp. 552-555 (1986).
Lezius et al., Eur. J. Biochem., vol. 3, pp. 85-94 (1967).
Brennan et al., Nucleic Acid Research, vol. 13, pp. 8665-8684 (1985).

(List continued on next page.)

Primary Examiner—John W. Rollins
Assistant Examiner—James O. Wilson
Attorney, Agent, or Firm—Banner, Birch, McKie & Beckett

[57] ABSTRACT

The present invention is directed to new artificial base pairs comprising complementary artificial purines and pyrimidines and methods of using artificial complementary base pairs.

18 Claims, 2 Drawing Sheets

OTHER PUBLICATIONS

Hofer et al., Nucleic Acid Research, vol. 9, pp. 753–766 (1981).

Mhaskar et al., J. Biol. Chem., vol. 259 pp. 11713–11717 (1984).

Jiricny et al., Nucleic Acid Research, vol. 14, pp. 6579–6590 (1986).

Birkofer et al., Angew. Chem., vol. 77, pp. 414–426 (1965).

Laland et al., Biochem. J., vol. 90, pp. 76–81 (1964).

Wempen et al., in Grossmen et al. (eds), "Methods in Enzym," XII, Part A, p. 75, Academic Press/1967).

Actoe et al., in Zorbek et al., (eds). "Synth Proc in Nuc. Acid Chem", vol. 1, p. 272 (1968).

Tong et al., J. Org. Chem., vol. 13 pages 859–862 (1967).

Kotick et al., J. Org. Chem., vol. 34, pp. 3806–3816 (1969).

Lee et al., J. Org. Chem., vol. 37, pp. 2923–2927 (1972).

Roark et al., in Townsend et al., (eds.), "Nucl. Acid Chem" Part 2 p. 583 (1978).

Narang et al., in Wu, ed., "Methods in Enzymology", vol. 68, p. 90 (1979).

Kazimierczuk et al., J. Am. Chem. Soc., vol. 106, pp. 6379–6282 (1984).

Girgis et al., Nucleic Acid Research, vol. 15, pp. 1217–1226 (1987).

Fox et al., J. Am. Chem. Soc., vol. 80, pp. 1669–1675 (1958).

Gough et al., Nucleic Acid Research, vol. 6, pp. 1557–1570 (1979).

Casadaban et al., Proc. Nat. Acad. Sci. USA, vol. 76 pp. 4530–4533 (1979).

Yanisch-Perron et al., Gene, vol. 33, pp. 103–119 (1985).

Altematt et al., Helvetica Chimica Acta, vol. 68, pp. 475–483 (1985).

Rappaport, Nucleic Acid Research, vol. 16, pp. 7253–7268 (1988).

ARTIFICIAL DNA BASE PAIR ANALOGUES

The present application is a continuation-in-part of application Ser. No. 99,744, filed in the United States Patent and Trademark Office Sep. 22, 1987, now abandoned.

FIELD OF THE INVENTION

This invention is directed to new DNA base pair analogs and methods of making and using their analogs.

DESCRIPTION OF THE BACKGROUND ART

The advent of simple and rapid synthetic procedures for the synthesis of oligodeoxynucleotides from protected deoxynucleotides has resulted in a substantial number of physical and biological investigations of mismatch base pairs (Aboul-ela, et al, *Nucleic Acid Research*, 14:4811, 1985) and investigations of base pairs where one base is an analog (Jiricny, et al., *Nucleic Acid Research*, 14:6579, 1986).

The question of whether it is possible to design a pair of bases that could function as an additional complementary base pair in the genetic apparatus of cells has not been explored. The criteria used to design complementary base pairs should address the issues of stability, biochemical pathways for the synthesis of (deoxy)nucleoside triphosphates from bases and/or nucleosides, analog inhibition of essential metabolic pathways, DNA and RNA polymerase utilization of the (deoxy)nucleoside triphosphates, DNA polymerase error frequency and error correction, and the issue of mismatch base pair repair.

Earlier very little structural or quantitative data was available about polymerase error frequency (Goodman, et al., *Journal of Molecular Biology*, 88:423,1974), polymerase error correction, and mismatch base pair repair. These issues have been clarified significantly (Kramer, et al., *Cell*, 38:879, 1984). An important caution for the designer of complementary base pairs is that the relationship between the ultimate fidelity of reproduction of genetic information and the strength of interaction between different bases is not physically unique.

SUMMARY OF THE INVENTION

It is an object of the invention to provide new oligodeoxynucleotide base pairs comprising an artificial purine paired with an artificial pyrimidine wherein the artificial purine has 2,6, substituents that establish an interaction with 2,4 substituents of the paired artificial pyrimidine such that the structural integrity of the double strand is maintained.

It is an additional object of the present invention to provide base pairs of artificial purines paired with artificial pyrimidines wherein the artificial purines have 2,6 substituents selected from H,O,S and NH$_2$ and the complementary base is an artificial pyrimidine having 2,4 substituents selected from H,O,S and NH$_2$, such that the 6 position of the artificial purine interacts with the 4 position of the artificial pyrimidine as a first base interaction and the 2 position of the artificial purine interacts with the 2 position of the artificial pyrimidine as a second base interaction, and wherein at least one of the first or second base interactions is H-S, and further such that when the base pairs are present in a double stranded genetic sequence containing A, T, C and G the structural integrity of the double strand is maintained.

It is a further object of the invention to provide new compounds which can be used as artificial purines and artificial pyrimidines for integration into a double stranded genetic sequence as complementary base pairs.

In accordance with this invention, there are provided artificial pyrimidines of the formula:

wherein R1 is hydrogen, sulfur, oxygen, or amino, R2 is hydrogen, oxygen, sulfur, or amino, and R3 is hydrogen, halogen, —SCH$_3$, —OH, hydroxymethyl, alkoxyl, cyano, methylamino, nitro, or unsubstituted, or halogen substituted hydrocarbon groups 1-3 carbon atoms long. Also included are position 5 and/or 6 aza derivatives and position 1 deaza derivatives of these compounds.

Further in accordance with the invention, there are provided artificial purines of the formula:

wherein R1 is hydrogen, sulfur, oxygen or amino, and R2 is hydrogen, sulfur, oxygen or amino. Also in accordance with the invention are included 3-deaza and 7-deaza derivatives of these compounds.

The present invention thus relates to double stranded genetic sequences having base pairs of adenine (A) and thymine (T), cytosine (C) and guanine (G), as well as base pairs of artificial purines paired with artificial pyrimidines wherein the artificial purines have 2,6 substituents that establish an interaction, selected from hydrogen bonding and hydrophobic interactions, with 2,4 substituents of the paired artificial pyrimidines such that the structural integrity of the double strand is maintained. As occurs with natural base pairs, the artificial base pairs of the invention have a hydrogen bond between the 1-purine and 3-pyrimidine positions. In the bas pairs of the invention, at least one substituent in the 2, 6 purine or 2, 4 pyrimidine position is sulfur and the substituent complementary to the sulfur is hydrogen. Desirably, the groups which provide the interaction between complementary artificial base pairs are sulfur and hydrogen; oxygen and hydrogen; oxygen and amino; or hydrogen and hydrogen.

The artificial purines and artificial pyrimidines and their use as paired bases represent a significant advantage in genetics. Although some artificial purines and artificial pyrimidines were known, these prior art molecules were never employed for the formation of stable base pairs. In fact, prior art artificial molecules were employed to inhibit standard base, nucleoside, or nucleotide synthesis or to de-stabilize the target DNA as, for example, in their use as anti-cancer agents. In contrast, the paired artificial purines and artificial pyrimidines of the invention not only allow the maintenance of a stable DNA duplex, but also, these artificial bases pairs will interact preferentially with each other even in the presence of naturally-occurring base pairs.

A societal concern which has arisen with the advent of recombinant DNA technology is the escape of genetically altered organisms and the possibly harmful affects they might have on the environment. If a recombinant organism incorporating the artificial base pairs of the invention were to escape, or be released into the environment, it would be unable to replicate due to the absence of the necessary artificial purine and artificial pyrimidine bases or nucleoside comprising the artificial base pair.

Using the artificial base pairs of the invention it is possible to design organisms that, even if they were to be released or escape into the environment, would be unable to replicate. Since the artificial base pairs of the invention cannot be synthesized by any natural organism or by the recombinantly modified host organism, the incorporation of the artificial base pairs of the invention into the genome of the recombinant organism will prevent replication unless the artificial bases are supplied exogenously as, for example, in the growth medium. This is because the host organism does not have the necessary biosynthetic machinery to allow it to synthesize the artificial base pairs of the invention from other substrates, making the organism totally dependent upon an external source of the artificial base pairs. Somewhat similarly, the rate of replication of an organism can be controlled by controlling the concentration of the artificial bases in the growth medium or available to the organism.

A further advantage of the artificial base pairs of the invention is that they can be used to produce recombinant organisms in which replication of the organism is synchronized from specific positions in the chromosome of the organism.

DESCRIPTION OF THE DRAWINGS

FIG. 1:

(a) A schematic representation of the base pair 5-methyl-2-pyrimidinone, left base, and 6-thioguanine, right base.

(b) The photograph shows the base pair 5-methyl-2-pyrimidinone/6-thioguanine derived from a cytosine/-guanine base pair. The cytosine/guanine base pair is three base pairs from the end of an oligodeoxynucleotide duplex determined by X-ray crystallography (Dickerson, et al., *Journal of Molecular Biology*, 149: 761, 1981). The amino group of cytosine, the left base, was replaced with a hydrogen, bond length 1.09 A. The 5-methyl group is not shown. The oxygen of guanine, the right base, was replaced with a sulfur, bond length 1.7 A. No other changes were made. The dots indicate the extent of the van der Waals radii for sulfur, 1.8 A, and hydrogen, 1.2 A.

DETAILED DESCRIPTION

Figure 1A:
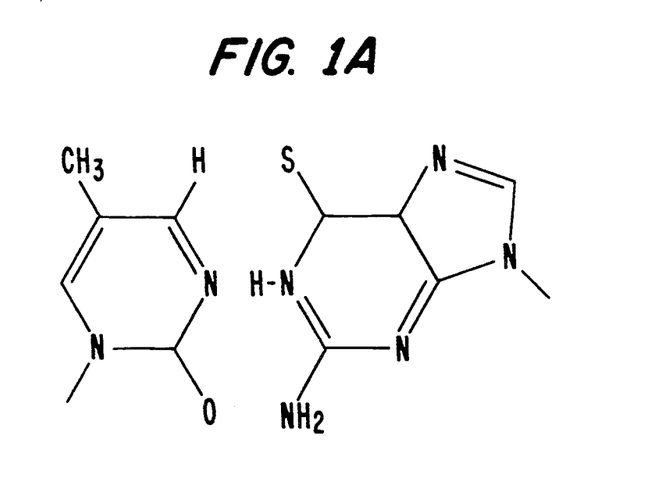
Figure 1B:
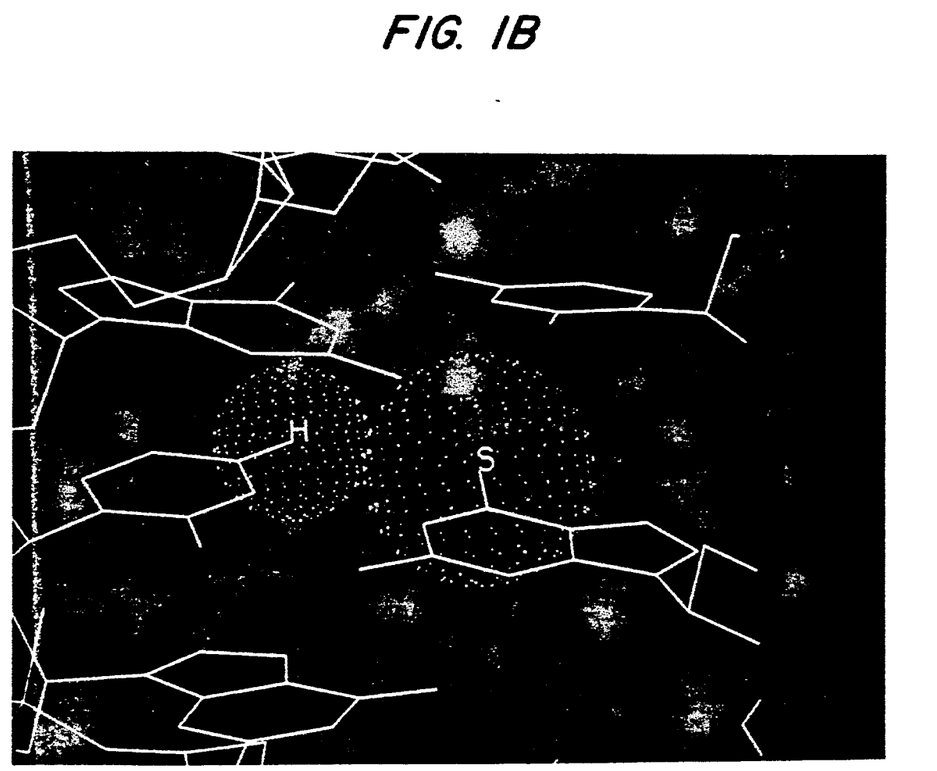

The base pairs of the invention desirably should satisfy certain conditions: 1. The base pair should contribute to the stability of the duplex molecule. 2. There should be a significant free energy discrimination against base pairing between the new and standard bases when compared to either the standard base pairs or the new base pair.

The primary chemical and biological rationalizations underlying the choice of the base pairs are: 1. The hydrogen bond between the 3-nitrogen of the pyrimidine and the 1-nitrogen of the purine is retained so that the net change in hydrogen bonds of these positions and water molecules will not change with duplex formation.

2. Spectroscopy in the gas phase suggested that the hydrogen-bond force constant of sulfur is one half that of oxygen and that the most stable angle between the X-H axis and the symmetry axis of the sulfur bonds is 90 degrees instead of the 45 degrees of oxygen.

Other substituents can be substituted at various positions as long as the substituent does not disrupt or destabilize the basic function of the double standard genetic sequence molecule.

The selection of acceptable artificial purines and complementary artificial pyrimidines as base pairs is influenced by such bonding factors as, for example, hydrogen bonding and hydrophobic interactions as well as steric factors. For example, the artificial pyrimidines of the invention do not utilize the iodine atom at the 4 position because of the steric stability problems of ten created by this large atom.

The ratio of the association constant of the duplex with the base pair G/T compared to A/T, Table IV, is 1/3, a value that is a factor of 9 greater than the value determined in 1 M NaCl by About-ela, et al. (*Nucleic Acid Research*, 13:4811, 1985). Their value is based on the interpretation of optical density changes during melting within the framework of a two state model. Markey, et al. (*Biopolymers*, 22:1247, 1983) have shown that the caloric enthalpy is different than the Van't Hoff enthalpy as the ionic strength increases. The result indicates the two state model may introduce a significant error in the calculation of association constants. A direct NMR measurement at low ionic strength and 15° C. of the association constants between 7-mers with a G/T substituted for a G/C gave a value of 1/25 (Salisbury, et al., *Journal of the Chemical Society, Chemical Communications*, 14,985,1985). The equivalent ratio from Table IV is 1/42 at 19° C. The very strong dependence of stability on the detailed sequence when G/T base pairs are present is illustrated by crystals of a duplex composed of oligodeoxynucleotide G-G-G-G-T-C-C-C being stable at room temperature (Kneale, et al., *Journal of Molecular Biology*, 186:805,1985) while crystals of G-G-G-G-C-T-C-C melted above 6° C. (Hunter, et al., *Journal of Molecular Biology*, 190:605,1986). On general grounds it would be expected that values based on a two state model of melting would overestimate differences in stability while an estimate based on enzymatic ligation of duplexes might underestimate the difference because duplexes with only partial base pairing may function as a substrate. The similarity between the result of the enzymatic ligation and the result of the NMR method is reassuring.

Using a template oligodeoxynucleotide containing the base 2-pyrimidinone and the Klenow fragment of DNA polymerase I, Charczuk, et al. (*Nucleic Acid Research*, 14:9530,1986) have presented preliminary evidence that no standard nucleotide is incorporated across from 2-pyrimidinone.

With the exception of the G/T base pair the results of Table IV are consistent with the results of Aboul-ela, et al. (ibid). Both show the standard base pairs confer much greater stability than mismatched pairs of the standard bases. The base pair 6-thioguanine/5-methyl-2-pyrimidinone conferred a stability that was nearly equal to the standard base pair adenine/thymine. The mismatch base pair that had the greatest stability, guanine/5-methyl-2-pyrimidinone, apparently does not have the appropriate geometry for significant polymerization to occur with DNA polymerase I (Charlczuk, et al., ibid). The results suggest that the base pair 6-thioguanine/5-methyl-2-pyrimidinone has the necessary physical characteristics to be a useful complementary base pair.

Experiments with *Escherichia coli* C600 using either tritium labeled 6-thioguanine or deoxyribosyl-5-methyl-2-pyrimidinone showed that the (deoxy)nucleoside triphosphates were synthesized. Extremely small amounts of the separate bases were incorporated into the DNA.

In addition to the matters discussed above, the (deoxy)nucleoside triphosphates should be substrates for both RNA and DNA polymerases with templates containing the complementary base and the analogs and their derivatives should not be significant inhibitors of essential metabolic pathways. Mismatches between the new and the standard bases should be enzymatically correctable.

The artificial pyrimidines can also be either 5 or 6 aza derivatives. If position 5 is carbon it can have substitution of such radicals as hydrogen, halogen, —SCH₃, —OH, alkoxyl, cyano, methylamino, hydroxymethyl, nitro, and unsubstituted or halogen substituted hydrocarbon groups 1-3 carbon atoms long. The artificial purines can be also the 3-deaza or 7-deaza derivatives.

At least one of the 2, 6 purine or 2, 4 pyrimidine substituents is sulfur. Whenever a thioketo group is present at a position on one member of the artificial base pair, a hydrogen is present at the complementary position of the other member of the artificial base pair. Desirably, in addition to the sulfur-hydrogen complementary substituents, the artificial base pairs will have oxygen-hydrogen, or oxygen-amino complementary substituents. The 2, 6 purine substituents can be the same or different, for example, sulfur and oxygen, sulfur and amino, or sulfur and sulfur. Similarly, the 2, 4 pyrimidine substituents can be the same or different.

Suitable artificial base pairs are:
4-thioketo-pyrimidine and 2-thioketo-purine
2-amino-4 thioketo-pyrimidine and 2-keto-purine
2-thioketo-pyrimidine and 6-thioketo-purine
2-thioketo-4-amino-pyrimidine and 6-keto-purine
2-keto-4-thioketo-pyrimidine and 2-amino-purine
2-thioketo-4-thioketo-pyrimidine and purine
2-keto-pyrimidine and 2-amino-6-thioketo-purine
4-thioketo-pyrimidine and 2-keto-purine
4-keto-pyrimidine and 2-thioketo-purine
2-keto-pyrimidine and 6-thioketo-purine Other suitable artificial base pairs wherein the pyrimidines can also be the 1-deaza derivatives (pyridine derivatives), but the purines can not be 3-deaza derivatives are:
2-amino-pyrimidine and 2-keto-6-thioketo-purine
pyrimidine and 2-thioketo-6-thioketo-purine
4-amino-pyrimidine and 2-thioketo-6-keto-purine The artificial purines and pyrimidines used in the base pairs can be synthesized using techniques know to those of ordinary skill in he art (see *Nucleic Acid Chemistry*, Townsend, et al., Eds., Part 1 (1978), 2 (1978) and 3 (1986); Zorbach, et al., in *Synthetic Procedures in Nucleic Acid Chemistry*, Vol. 1, (1965). The appropriate deoxynucleoside of a given base can be synthesized from 2-deoxy-3, 5 -di-O-p-toluoyl-D-erythro-pentosyl chloride (Bhat, in *Synthetic Procedures in Nucleic Acid Chemistry*, Zorback, et al., Eds., Vol. 1, p. 521, 1968) and the appropriately protected base by either: 1. the silyl-mercuric method in solution (Birkofer, et al., *Agnew. Chem.*, 77:414,1965) or by fusion (Kotick, et al., *Journal of Organic Chemistry*, 34:3806, 1969); or 2. the stereospecific sodium salt method (Kazimierczuk, et al., *Journal of The American Chemical Society*, 106:6379, 1984).

Synthesis of the 3- and 7-deaza purine deoxynucleosides can be done using the sodium salt method (Kazimierczuk, et al., ibid) and the appropriate derivatives (Givgis, et al., *Nucleic Acid Research*, 15:1217, 1987). The synthesis of pyrimidine c-deoxynucleosides can be done using methods analogous to those described by Sato et al. (in *Nucelic Acid Chemistry*, Townsend, et al., Eds., Part 3, p. 81, 1978) using nucleosides.

The synthesis of 1-deaza pyrimidine derivatives (pyridine derivatives) can be done using standard organic chemistry. Pyridine derivatives will react with 2-deoxy-3,5-di-O-p-toluoyl-D-erythro-pentosyl chloride in the presence of a Lewis acid, AlCl₃ or BF₃, or silver perchlorate to give an electrophilic substitution at the 3 position of the pyridine derivative.

In those instances where both the alpha and beta anomers of the artificial deoxynucleosides are produced, they can be separated by such standard techniques as, for example, differential crystallization (in *Nucleic Acid Chemistry*, Townsend, et al., Eds., Part 2, 1978) or column chromatography (lee, et al., *J. Org. Chem.* 37:2923, 1972).

The transformation of host organisms by incorporation of the artificial base pairs of the invention can be accomplished by the uptake of DNA in the form of linear segments or as part of a plasmid or phase capable of integrating its nucleic acid into the host genome. Techniques for host cell transformation are well known to those of skill in the art and will not be further described.

It is preferred that the DNA contain a multiplicity of artificial complementary base pairs. Further, it is preferable that the DNA sequence containing the artificial base pairs integrate into a region of the host cell genome in a location such as, for example an intron, where significant disruption of host genetic expression or viability will not be significant.

Eucaryotic and procaryotic organisms, both aerobic and anaerobic, can be used as hosts for transformation with the artificial base pairs of the invention. The transformed organisms can be cultured in aqueous media in a suitable fermentation vessel. Typically, the aqueous media will be, for example, maintained at about 37° C., and near neutral pH and contain appropriate nutrients such as carbohydrate or glycerol as a carbon source, nitrogen sources such as ammonium sulfate, potassium sources such as potassium phosphate, trace elements, magnesium sulfate and the like. Once again, culture media and conditions will vary with the host organism, but are well known in the art.

After a host organism has been constructed which contains the synthetic base pairs of the invention, it is then possible to regulate replication of the host cell by controlling the concentration of artificial base pairs in the culture media. The appropriate concentration of base pairs may vary with the particular organism a with the number of pairs of bases in the host genome. The optimal concentration of synthetic base pairs in the culture media would be readily determinable by one of skill in the art.

The artificial base pairs of the invention also allow recombinant organisms to be produced wherein replication of the organism is synchronized. This technique can be achieved using standard methods of restriction enzymes and ligation to introduce a sequence of artificial base pairs such as, for example, the Mu phage mutant Mud I (lac, ap) (Casadaban, et al., *Proceedings of the National Academy of Sciences*, 76:4530, 1979). The Mud genome integrates almost anywhere in the *E. coli* chromosome and clones with Mud 1 integrated in a particular region can be selected (Casadeban, et al., ibid). In the absence of an external source of artificial bases, replication will stop when the replication complex reaches the artificial base pair in the chromosome. Eventually, all of the cells in the culture will arrive and stop replication at this unique site in the chromosome. The addition of the artificial bases will start replication of all of the cells at the same time and at the same place. In addition, this method is appropriate for any procaryote that has an appropriate vector which is integrated into the host chromosome. Likewise, since there are many unique sites of initiation of replication in the eucaryotic chromosome, the use of an integratable vector carrying the artificial base pairs of the invention will allow control of the synthesis of restricted intervals of the eucaryotic chromosome in the same manner as described above for procaryotes.

The above discourse generally describes the present invention. A more complete understanding can be obtained by reference to the following specific examples which are provided herein for purposes of illustration only and are not intended to limit the scope of the invention.

EXAMPLE 1

SYNTHESIS OF 6-THIOGUANINE/5-METHYL-2-PYRIMIDINONE BASE PAIR

A. Materials

The chemicals employed and their sources were: betadeoxynucleosides (Sigma), benzenethiol (Eastman), cetyltrimethylammonium bromide (Aldrich), 2-chlorophenyl-dichlorophosphate (Aldrich), 4,4'-dimethoxytrityl chloride (Aldrich), long chain alkylamine controlled pore glass (Pierce), 1-(mesity-lene-2-sulfonyl)-3-nitro-1,2,4-triazole (Aldrich), mercury (II) cyanide (Aldrich), 1-methylimidazole (Aldrich), 2-nitrobenzaldoxime (Aldrich), p-nitrophenyl acetate (Sigma), silver carbonate (Aldrich), silica Woelm TSC (INC Nutritional Biochemical). All solvents were redistilled and stored under appropriate anhydrous conditions (Sproat, et al., in Gait, M. J. (Ed.), *Oligonucleotide Synthesis*, IRL Press, Oxford, 1984).

Enzymes employed and their sources were: polynucleotide kinase (Bethesda Research Labs), snake venom phosphodiesterase (Sigma), T4 DNA ligase (Bethesda Research Labs), Sal I (New England Biolabs.).

B. Synthesis of deoxynucleosides 1. 2-amino-9-(2-doxy-beta-D-ribofuranosyl)-9H-purine-6-thiol (beta-deoxy-6-thioguanosine). The beta anomer of 2-acetoamido-6-chloro-9H-(2-deoxy-3,5-di-o-p-toluoyl-D-ribofuranosyl) purine was prepared by a known procedure (Roark, et al., Townsend, L. B. and Tipson R. S. (Eds.), *Nucleic Acid Chemistry*, John Wiley and Sons, Part 2, 583, 1978). The protected beta anomer of the 6-chloro derivative was deprotected and thiated according to Acton, et al. (in *Synthetic Procedures in Nucleic Acid Chemistry*, Zorback, et al., Eds., Vol. 1, 272, 1968). The resulting material, after crystallization from hot water, had the expected ultravioletvisible spectrum (Tong, et al., *Journal of Organic Chemistry*, 32:859, 1967).

2. 1-(2-deoxy-beta-D-ribofuranosyl)-5-methyl-2-pyrimidinone (beta-deoxyribosyl-5-methyl-2-pyrimidinone). 4-thiothymidine was prepared by a published procedure (Wempen, et al., in Grossmen, L., and Moldare, K. (Eds.), *Methods in Enzymology*, Academic Press, XII, Part A, 75, 1967). Deoxyribosyl-5-methyl-2-pyrimidinone was prepared from the 4-thiothymidine by reduction with Raney nickel. 5.9 gm (22 mmole) of 4-thiothymidine was added to 180 ml of distilled water and 60 ml of ethyl alcohol in a flask with a reflux condenser. 24 gm of Raney nickel was added and the solution heated to reflux. For the highest yields a 4-thiothymidine solution was triturated with each Raney nickel preparation and the optical density of a sample in 0.1 N HCl was determined at 260, 322, and 334 nanometers. The optical density decreased at all three wave lengths. The reaction was terminated when the optical density at 322 nanometers was equal to or greater than the optical density at 334 nanometers. The decrease in optical density at 334 nanometers from the initial solution was about a factor of 6 for the maxim yield. The reaction was followed with silica gel thin layer chromatography (TLC) using isopropanol. A blue fluorescent spot, characteristic of the compound, appeared with an Rf of 0.35. The initial greenish solution became a very light yellow by the end of the reaction. Because other products where formed the reaction was not run until all of the 4-thiothymidine was used. The suspension was filtered hot and the Raney nickel boiled with 150 ml of water. The solution was filtered hot. The combined filtrates were evaporated. Deoxyribosyl-5-methyl-2-pyrimidinone was purified by dry column chromatography with Woelm silica III. 10 ml of methanol was added to the solid from the Raney nickel reduction. 3.7 ml of the clear solution was added to 3.7 gm of Woelm silica III and air dried. The dried silica with the deoxyribosyl-5-methyl-2-pyrimidinone was added to the top of a column of dry Woelm silica, 20 inches long by 1 inch diameter, contained in nylon tubing. Isopropanol was the solvent. The solvent front was allowed to reach the bottom of the silica column before terminating the chromatography. The nylon tubing was cut into 1 inch sections and the silica in each section was extracted with 10 ml of methanol. Samples from each section were run on silica gel TLC with isopropanol. The methanol extracts were pooled from those sections that showed only the fluorescent spot with Rf 0.35. The pooled silica from the appropriate sections was extracted again with methanol and pooled with the first extraction. After filtration the methanol was evaporated to a small volume and the remaining fine particles of silica were removed by centrifugation. The remaining methanol was evaporated and the residue dissolved in 10 ml of hot ethyl alcohol. The solution was placed at $-20°$ C. Crystals formed overnight. The yellow supernatant was decanted and the crystals washed in cold ethanol. The volume was reduced to 4 ml and placed at $-20°$ C. More crystals formed. Silica gel TLC revealed a contamination of less than 5%. The ultraviolet-visible spectrum of a solution of the crystals was equivalent to the literature spectrum (Laland, et al., *Biochemical Journal*, 90:76, 1964). The overall yield from 4-thiothymidine to the final product was about 25%.

C. Synthesis of protected deoxynucleosides

5'-0-4,4'-dimethoxytritylthymidine, N-benzoyl-5'-0-4,4'-dimethoxytrityldeoxycytidine, N-benzoyl-5'-0-4,4'-dimethoxytrityldeoxyadenosine, and N-isobutyryl-5'-0-4,4'-dimethoxytrityldeoxy-guanosine were synthesized by standard methods (Narang, et al., in *Methods in Enzymology*, Wu, Ed., Vol. 68, 90, 1979).

1. N-benzoyl-deoxy-5-thioguanosine. Preliminary experiments indicated that the N-isobutyryl and N-acetyl derivatives were too labile during alkaline hydrolysis to allow a significant yield of the N-protected nucleoside. To 0.5 gm (1.7 mmole) of deoxy-6-thioguanosine, that had been repeatedly dried by evaporation of anhydrous pyridine, was added 3.3 ml of anhydrous pyridine and 6.6 ml of redistilled chloroform. At 4° C., 4.7 ml of redistilled chloroform containing 1.35 ml (12 mmoles) of benzoyl chloride was added dropwise with stirring in a flask with a $CaCl_2$ drying tube. After the addition of the benzoyl chloride all of the deoxy-6-thioguanosine went into solution and the solution was yellow. The solution was allowed to come to room temperature and was stirred for three hours. Silica gel TLC of a sample of the reaction with methanol/chloroform (0.5:9.5 v/v) showed one s pot with UV absorption that turned dark brown on exposure to acid and heat. The spot was at the solvent front. The reaction solution was poured into 60 ml of ice. After melting, 10 ml of chloroform was shaken with the aqueous emulsion. After separation of the phases, the organic phase contained all the yellow color. The organic phase was washed three times with 20 ml of water. The organic solution was dried with sodium sulfate and evaporated to an oil.

19 ml of pyridine was added to the oil. A clear solution was obtained. 1.8 ml of water was added and then 19 ml of methanol was added. The solution was placed at 4° C. and 2 N NaOH was added slowly until a pH reading of 12.4–12.5 was reached. The pH was maintained around 12.4 by the addition of 2 N NaOH. The hydrolysis was followed with silica gel TLC using methanol/chloroform (1.5:8.5 v/v). A majority of the UV absorbing material was present in one spot with an Rf of 0.3. The Rf of deoxy-6-thioguanosine was 0.19. Some care was necessary with the addition of the NaOH and the time in order to avoid a significant production of deoxy-6-thioguanosine. The reaction was stopped by lowering the pH to a reading of 7.8 with 20% acetic acid. A considerable loss was sustained if an exchange resin was used for the neutralization. The solution was evaporated to an oil.

Pilot experiments demonstrated that the difference in solubility of the N-benzoyl derivative and the di, tri, tetra benzoyl derivatives in hot water provided a convenient method of purification. 600 ml of water was added to the oil and heated to 70° C. with stirring. Liquid was decanted from the insoluble material and placed at 4° C. A precipitate formed and was recovered by filtration. The aqueous solution was evaporated to 250 ml and a second precipitate recovered by filtration. Silica gel TLC of the combined precipitates showed more than 90% was the N-benzoyl derivative.

An equivalent separation procedure was to dissolve the oil in 20 ml of chloroform and to extract repeatedly the chloroform with a weakly basic solution of $NH_4OH$, pH 10.

The identification of the 0.3 Rf spot with N-benzoyl-deoxy-6-thioguanosine was based on a quantitative determination of the amount of benzoic acid recovered after complete alkaline hydrolysis and a characteristic shift of the peak of absorption from approximately 340 nanometers to 320 nanometers when the pH was changed form 5 to 12. A shift does not occur if a thioester is present.

2. N-benzoyl-5'-0-4,4'-dimethoxytrityl-deoxy-6-thioguanosine. 125 mg (0.32 mmole) of the N-benzoyl-deoxy-6-thioguanosine was dried by repeated evaporation of anhydrous pyridine. 1.25 ml of anhydrous pyridine was added and 172 mg (0.5 mmole) of 4,4'-dimethoxytrityl chloride was added at room temperature. After two hours silica gel TLC with chloroform showed no N-benzoyl-deoxy-6-thioguanosine was present. 3 ml of methanol was added. After 15 minutes the solution was added to 6 ml of cold water. The aqueous solution was extracted with 5 ml of chloroform. The chloroform was washed with 5 ml of water and the organic phase was dried with sodium sulfate. The solution was evaporated to 2.5 ml and the chloroform solution was streaked on 4 silica gel preparative plates, 1000 u, 20×20 cm with a fluorescent indicator. Methanol/chloroform (1:9 v/v) was the solvent. The dimethoxytrityl derivative was located by running an analytical TLC and determining which UV absorbing spot turned orange on spraying with acid. The bands of silica containing N-benzoyl-5'-0-4,4'-dimethoxytrityl-deoxy-6-thioguanosine were scraped off and eluted with methanol. The silica particles were removed by centrifugation. The methanol solutions were pooled and evaporated to dryness.

3. 5'-0-4,4'-dimethoxytrityl-deoxyribosyl-5-methyl-2-pyrimidinone. 0.639 gm (2.5 mmole) of beta-deoxyribosyl-5-methyl-2-pyrimidinone was dried by repeated evaporation of anhydrous pyridine. 8 ml of anhydrous pyridine and 1.1 gm (3.2 mmole) of 4,4-dimethoxytrityl chloride was added with stirring at room temperature. All the material was in solution 30 minutes. After 45 minutes a sample was analyzed by silica gel TLC with methanol/chloroform (1:9 v/v) and indicated the reaction was complete. The derivative had an Rf of 0.37. Methanol (1.2 ml) was added and stirred for 15 minutes. The solution was poured into 20 ml of ice cold water. After standing overnight at 4° C., the aqueous phase was decanted from the light yellow gum. The gum was dissolved in 10 ml of ethyl acetate. The aqueous phase was extracted with 8 ml of ethyl acetate and combined with the initial ethyl acetate solution. The ethyl acetate solution was washed with 7 ml and each of $NaHCO_3$, water, 1m NaCl. The ethyl acetate solution was dried with sodium sulfate, decanted, and evaporated to a gum. The gum was dissolved in 4 ml of chloroform and added to a short silica column, 20×75 mm. A solution of 0.5% triethylamine in chloroform was run through the column until yellow color started to come off. The solvent was changed to methanol/chloroform (0.2:10 v/v) and 10 ml fractions collected. The fractions were monitored at 329 nanometers for the deoxyribosyl-5-methyl-2-pyrimidinone derivative. Samples of the fractions were analyzed on silica gel TLC with methanol/chloroform (1:9 v/v). The fractions that appeared pure were pooled and evaporated under vacuum.

4. Triethylammonium(5'-0-4,4'-dimethoxytrityl-protected-deoxynucleoside-3'-0-(2-chlorophenyl phosphate). All the compounds were prepared by standard methods (Narang, et al., in Wu, R. Ed., *Methods in Enzymology*, 68:90, 1979). It was essential to check all susceptible solvents for peroxides when carrying out the procedures with deoxy-6-thioguanosine.

D. Synthesis of oligodeoxynucleotides

The phosphotriester method (Sproat, et al., ibid) was used with solid supports of polystyrene or controlled pore glass. The final synthesis of oligodeoxynucleotides containing 6-thioguanine and 5-methyl-2-pyrimidinone used a glass support.

For the synthesis of each of the oligodeoxynucleotides containing 6-thioguanine and 5-methyl-2-pyrimidinone 16 mgs of long chain alkylamine controlled pore glass was used with 0.38 moles of 5'-0-4,4'-dimethoxytrityl-2'-deoxyguanosine-3'-0-succinate attached. The reaction solutions were prepared by adding 80 ul of anhydrous pyridine to 10 umoles of dry, protected nucleotide. The prydiene solution was added to 13 mg of 1-(mesitylene-2-sulfonyl)-3-nitro-1,2,4-triazole and after one minute 8 ul of 1-methyl-imidazole was added. The solution was added to the solid support under nitrogen at room temperature. The reaction was terminated after 30 minutes by washing the solid support with anhydrous pyridine and dichloromethane. The dimethoxytrityl group was removed with 2% trichloroacetic acid in dichloromethane. The support was washed with dichloromethane and then anhydrous pyridine. The next cycle of nucleotide addition was started.

E. Cleavage, Deportection, and Regeneration

The alkaline susceptibility of 6-thioguanine and 5-methyl-2-pyrimidinone precluded the use of the standard aqueous methods of cleavage from the solid support and the deportection of the oligodeoxynucleotides. Model experiments demonstrated that $NH_4OH$ solutions converted deoxy-6-thioguanosine to deoxyguanosine and several minor components within several hours at a temperature of 50° C. Deoxyribosyl-5-methyl-2-pyrimidinone was converted to another component within minutes on exposure to strong alkaline conditions at room temperature and this compound changed over longer times into several components. Model experiments demonstrated that the deoxy-3'-0-succinate bond and the o-chlorophenylphosphate bond were cleaved slowly with syn-2-nitro-benzaldoximate in anhydrous pyridine. The isobutyryl and benzoyl groups were removed by ammonolysis in anhydrous methanol.

Model experiments with deoxy-6-thioguanosine demonstrated that 1-(mesitylene-2-sulfonyl)-3-nitro-1,2,4-triazole reacted rapidly with the 6-thio group under the conditions of the reaction to add protected nucleotide to the oligodeoxynucleotide. Deoxy-6-thioguanosine was completely regenerated from the mesitylene sulfonyl adduct by benzenethiol in pyridine. As expected, the reaction with mercapotoethanol was very slow and gave more than one product.

The glass support with the oligodeoxynucleotide was dried in vacuum over $P_2O_5$ and KOH. 0.45 ml of anhydrous pyridine with 55 ul of benzenethiol (1 M) was added to the glass under dry nitrogen gas. The reaction vial was tightly closed and left at room temperature for eight hours. The solution was removed and the glass support was washed four times with 1 ml of dichloromethane. The remaining dichloromethane was removed by vacuum and the glass support dried over $P_2O_5$ and KOH.

16.6 mg (100 umole) of syn-2-nitrobenzaldoxime was dried by repeated evaporation of anhydrous pyridine. 200 ul of anhydrous pyridine was added in a nitrogen atmosphere to dry nitrobenzaldoxime and then 36 ul of dry tetramethylguanidine was added. The solution and glass support were sealed in a vial under nitrogen and kept at room temperature for 5 days. The extent of the release of the oligodeoxynucleotide into the solution was followed by assaying 1 ul of the solution for the dimethoxytrityl group. 27 mg of p-nitrophenylacetate was added under nitrogen to the nitrobenzaldoximate solution to use up the remaining oximate ions. After three hours 1 ml of pyridine containing 10 ul of 20% acetic acid was added. The pH was measured by paper to make sure the pH was between 7 and 8. The solution was removed from the glass support and 1 ml of 50% aqueous pyridine was added to the glass support and the suspension shaken for 30 minutes. The solution was removed and combined with the initial pyridine solution. The solution was evaporated to dryness.

1 ml of dry methanol containing 9 mg (25 mmole) of cetyltrimethylammonium bromide was added to the dried N-protected oligodeoxynucleotide. The solution was saturated with $NH_3$ gas at 4° C. the test tube was stoppered tightly and securely, and placed at room temperature in the dark. After 7 days the test tube was opened at 4° C. and the solution evaporated at room temperature with dry nitrogen. The residue was dissolved in 1 ml of 80% acetic acid to release dimethoxytrityl group. After 20 minutes 1 ml of water was added and the aqueous solution was extracted five times with 2 ml of water saturated diethylether. The aqueous phase was evaporated to 200 ul. The solution was yellow. The solution was placed on a Dowex AG-50W × 2 column, 1.5 × 3 cm, that had been washed with 1 M $NH_4 HCO_3$ and then washed with distilled water. The column was eluted with distilled water and 0.5 ml fractions were collected. The fractions were monitored at 260 nanometers for the oligodeoxynucleotide and the appropriate fractions were pooled. The pooled fractions were evaporated to dryness and stored at −20° C.

F. Extinction Coefficients

The extinction coefficients at 260 nanometers of the oligodeoxynucleotides listed in Table I were calculated as follows: 1. An extinction coefficient of $10 \times 10^4 M^{-1}$ cm for A-T was calculated from the data listed by Soher (CRC Handbook of Biochemistry, 2nd Ed., Sober, H. A. (Ed.), The Chemical Rubber Company, Cleveland, OH). 2. The extinction coefficient of the $G^S$-T oligodeoxynucleotide was taken to be $10 \times 10^4 M^{-1}$ cm since the nucleoside of 6-thioguanine has an extinction coefficient at 260 nanometers of $8 \times 10^3 M^{-1}$ cm essentially independent of pH. 3. The extinction coefficient of the oligodeoxynucleotide containing 5-methyl-2-pyrimidinone was taken to be $9.2 \times 10^4 M^{-1}$ cm because the deoxynucleotide of 5-methyl-2-pyrimidinone has essentially no absorption at 260 nanometers (Laland, et al., ibid).

G. Ligation Assay

Labeled oligodeoxynucleotide concentrations varied between 0.1 and 0.01 uM. The carrier oligodeoxynucleotide was T-C-G-A-C-C-C-G-G-G and its concentration was 1 to 2 uM. The other components were 0.06 M Tris-HCl, pH 7.5, 5 mM $MgCl_2$, 5 mM dithiotrheitol, 0.5 mM ATP, and 0.06 to 0.005 Weiss units of T4 ligase per ul. The temperature was 19° C. The buffer, $MgCl_2$, dithiotrheitol, and oligodeoxynucleotides were combined and subjected to the following temperature cycle: 60° C.-65° C. for 5 minutes, room temperature for 15 minutes, and put on ice for 15 minutes. The 0.5 ml polypropylene test tubes were centrifuged to return all the water to the bottom before addition of ATP and the ligase.

H. Gel Electrophoresis

Preparative electrophoresis used 25% acrylamide gels (Gough, et al., Nucleic Acid Research, 6:1557, 1979). The gels were 0.2 × 13 × 29 cm. Before sample addition electrophoresis was carried out with $10^{-3}M$ glutatione in the upper buffer to remove peroxides and free radicals. $10^{-3}M$ glutatione was present in the sample solution. After the samples entered the gel, the current was reduced to 4 ma and electrophoresis was terminated when the dye, cyanol xylene, had traveled about 9 cm, 18-24 hours. UV absorbing bands of oligodeoxynucleotides were excised, ground into small pieces, and extracted several times with 0.1 M NH4HCO3 over several dyes.

I. HPLC Analysis

The nucleotides were analyzed on a weak anion exchange resin, Syn Chropak AX100, 250×4.6 mm, SynChrom Inc., Linden, IN., with a mobile phase of 0.05 F KH2PO4, pH 4.5. The nucleosides were analyzed on an octadecyl-silica column, 250×4.6 mm, with a mobile phase of 2.5% methanol and 0.02 F KH2PO4, pH 5.5. Methanol was changed to 10% for deoxyadenosine. Using this technique it was shown that the new nucleotide bases were present in the oligodeoxynucleotides.

EXAMPLE 2

PHYSICAL CHARACTERISTIC OF SYNTHETIC OLIGODEOXYNUCLEOTIDES

Table I lists the oligodeoxynucleotides synthesized by the solid phase phosphotriester method. The oligodeoxynucleotides were isolated by preparative electrophoresis in 25% acrylamide gels. The electrophoretic purity of the oligodeoxynucleotides was checked by labeling the 5' end with P32 phosphate and performing an electrophoretic analysis in 20%-25% acrylamide gels. The major P32 labeled component accounted for greater than 90% of the radioactivity and no other component amounted to more than 2% of the total radioactivity.

TABLE I

| OLIGODEOXYNUCLEOTIDES SYNTHESIZED | |
|---|---|
| Designation[a] | Sequence |
| #25 | T—C—G—A—C—G—G—A—T—C—C—G |
| MPO | T—C—G—A—C—G—G—A—(MPO)—C—C—G |
| 6TG | T—C—G—A—C—G—G—(6TG)—T—C—C—G |
| G | T—C—G—A—C—G—G—T—C—C—G |
| C | T—C—G—A—C—G—G—A—C—C—C—G |

[a]The bases 6-thioguanine and 5-methyl-2-pyrimidinone are designated 6TG or G[5] and MPO or T[H], respectively The number of nucleotide residues in the oligodeoxynucleotide was verified by labeling the 5' end with P32 phosphate and sequentially degrading the polymer with snake venom phosphodiesterase. The number of products obtained at various times of hydrolysis of the oligodeoxynucleotide was determined by electrophoresis in 20%-25% acrylamide gels at 50° C. and autoradiography.

The ultraviolet-visible absorption spectra of the poligodeoxynucleotides containing 6-thioguanine and/or 5-methyl-2-pyrimidinone showed significant absorption at neutral pH in the 310 to 350 manometer region over the absorption spectrum of the oligodeoxynucleotide with adenine and thymine at positions X and Y. 6-thioguanine has absorption peaks at 265 and 340 nanometers at neutral pH. Beta-deoxyribosyl-5-methyl-2-pyrimidinone has one absorption peak at 314 nanometers. In addition, beta-deoxyribosyl-5-methyl-2-pyrimidinone is fluorescent in ultraviolet light. The oligodeoxynucleotides containing 5-methyl-2-pyrimidinone were fluorescent under ultraviolet light.

Relative Stability of Base Pairs

The traditional method of determining the association constant of complementary oligodeoxynucleotides is to determine the optical density at 260 nanometers as a function of temperature. Unfortunately, this technique may lead to an erroneous interpretation. For oligodeoxynucleotides that have short runs of complementary sequences, less than about 16, the optical density transition region is quite broad and even assuming that the two state model is appropriate, the location of the temperature of the midpoint of the transition requires very good data. With the limited amounts of oligodeoxynucleotide synthesized in this initial study and the presence of one third of the sequence of the oligodeoxynucleotides as single stranded regions in the duplex structures, the determination of association constants by the analysis of optical density vs. temperature curves was not feasible. In place of temperature melting curves an enzymatic ligation procedure was developed to determine relative association constants.

The basic idea of the method was to measure the concentration of the duplex structure of a pair of oligodeoxynucleotides by determining the amount of ligation of the duplex to a carrier duplex, which was initially present in a much higher concentration than the concentration of the duplex of interest. The reason the ligation of the duplex to a carrier molecule was chosen instead of ligation of the duplex itself was the simplicity of the mathematical model. The mathematics of the self ligation is not simple except under very restrictive conditions. The amount of the duplex ligated to the carrier was followed by labeling one of the oligodeoxynucleotides of the duplex with P32 as a 5' phosphate. The carrier was phosphorylated with cold phosphate. Both the carrier duplex and the duplex of interest had 5' overhanging single stranded regions, T-C-G-A, that were complementary. Because of the possibility that single stranded oligodeoxynucleotides could be ligated to the carrier duplex, it was necessary to determine the extent of this reaction.

When the conditions listed in the next paragraph are realized the concentration of oligodeoxynucleotide 1 as a function of time is:

$$\ln[C(1,t)/C(1,0)] = -[K_s(1) + \epsilon K_d(1,2)C_d(2)]F(t) \quad \text{I.}$$

where $C(1,0)$ is the concentration at time zero of oligodeoxynucleotide 1, $C(1,t)$ is the concentration at time t, $K_d(1,2)$ is the association constant between oligodeoxynucleotides 1 and 2, $K_s(1)$ is the term that characterizes the rate of ligation of single stranded oligodeoxynucleotide 1 to the carrier molecules compared to the duplex, $C_d(2)$ is an average value of the concentration of oligodeoxynucleotide 2 during the time of reaction, $\epsilon$ is 1 when components 1 and 2 are different oligodeoxynucleotides and 2 when the oligodeoxynucleotides are the same, and $F(t)$ is a function of time which depends on the amounts of enzyme and carrier molecule but not on the amounts of oligodeoxynucleotides 1 and 2.

The experimental conditions necessary for equation I to be applicable are: 1. There is a sufficiently high concentration of the carrier so that the time course of the self ligation of the carrier molecules is not perturbed significantly by the amount of incorporation of the duplex. 2. The concentration of the duplex molecule is low so that the rate of ligation is proportional to the concentration of the duplex. 3. The concentration of the duplex is sufficiently low so that self ligation is insignificant compared to ligation with the carrier molecule. 4. The rates of association of the oligodeoxynucleotides and dissociation of the duplex are sufficiently fast so that equilibrium is maintained during the time of the reaction. 5. The Km's of the duplexes being compared are the same, that is, the significant characteristic is the 5' overlap region between the duplex and the carrier molecule and not the detailed sequence of the reset of the duplex molecule.

The results of the ligation of the self complementary oligodeoxynucleotide #25, Table I, to the carrier molecule are shown in Table II. A plot of the data from Table II clearly showed that the single stranded ligation predominated in the concentration range used. Duplex formation becomes detectable at a concentration of the oligodeoxynucleotide above $10^{-7}$ M. In addition, the results establish the important characteristic that the amount of labeled oligodeoxynucleotide ligated to the carrier was proportional to the amount present, a condition that is necessary for the validity of equation I.

Table III contains illustrative data that is used to determine the ratio between the association constant of the self complementary oligodeoxynucleotide, #25, and the association constant of the oligodeoxynucleotide pair 6TG and MPO, Table I. The data is analyzed using equation I. Line 4 has a concentration of #25 such that the ligation of the single strand predominated. Equation I becomes:

$$K_d(25)F(t) \ = \ -\ln[C(25,t)/C(25,0)] \qquad \text{II.}$$
$$= \ -\ln[6592/13361]$$
$$= \ .706$$

Line 3 has a concentration of #25 such that both duplex and single stranded molecules were ligated. Substitution into equation I gives:

$$K_d(25)F(t) \ + \ 2K_d(25,25)C_d(25)F(t) \ = \ -\ln[57240/126053] \qquad \text{III.}$$
$$= \ .789$$

$K_d(25)F(t)$ is known from equation II and using the equation:

$$C_d(2) = [C(2,0) - C(2,t)]/\ln[C(2,0)/C(2,t)]$$

$$C_d(25) = 1.2 \cdot 10^{-7} M.$$

Combining these results:

$$K_d(25,25)F(t) = 3.48 \cdot 10^5$$

When the same analysis is carried out with lines 1 and 2
$$K_d(6TG,MPO)F(t) = 2.38 \times 10^5 \qquad \text{V.}$$
and
$$K_d(25,25) = 1.5 K_d(6TG,MPO) \qquad \text{VI.}$$

Many of the measurements were performed at two different concentrations of enzyme between 0.6 and 0.05 Weiss units per 10 ul and the concentrations of all of the oligodeoxynucleotides were varied in different measurements. Relative association constants were not affected by different enzyme concentrations or by different oligodeoxynucleotide concentrations that allowed duplex formation to be detected. The independence of the relative association constants from changes in enzyme concentration and oligodeoxynucleotide concentration strongly suggests that the equilibrium condition between duplex and oligodeoxynucleotides was maintained during the course of the ligation. The independence of the relative association constants from the concentration of the oligodeoxynucleotides and the results shown in Table II indicate that the substrate concentrations were low compared to the $K_m$.

In the cases where the amount of labeled oligodeoxynucleotide that is ligated to the carrier molecules is small compared to the amount of the unligated oligodeoxynucleotide it might be objected that the uncertainty in counting the unligated oligodeoxynucleotide, C(t) is as large or larger than the amount ligated. The amount that is ligated is added to C(t) to obtain C(O). However, it is the quantity $$\ln[C(t)/C(O)]$$

that appears in the equations and when the difference C(O) − C(t) is small compared to C(O), $$\ln[C(t)/C(O)] = -[C(O) - C(t)]/C(O)$$

C(O) − C(t) is the amount of radioactivity actually measured. The uncertainty in C(t) appears only in C(O).

It was not possible to measure the relative association constant of the self complementary oligodeoxynucleotide 6TG-MPO, Table I, because every polynucleotide kinase preparation that was used to phosphorylate the 5' end contained an activity that rapidly cleaved the oligodeoxynucleotide.

The addition of the restriction endonuclease, Sal I, specific for the sequence used in the ligation, and sodium chloride to 150 mM to portions of the completed ligation reaction, resulted in a loss of ligated labelled oligodeoxynucleotide and an increase in unligated labeled oligodeoxynucleotide.

TABLE II

LIGATION OF OLIGODEOXYNUCLEOTIDE #25 TO CARRIER OLIGODEOXYNUCLEOTIDE

| concentration (um) | at 60 minutes (cpm) | Ligated at 60 minutes (cpm) |
|---|---|---|
| .05 | $9.2 \times 10^3$ | $5.8 \times 10^3$ |
| .025 | $4.5 \times 10^3$ | $3.5 \times 10^3$ |
| .0125 | $2.7 \times 10^3$ | $1.4 \times 10^3$ |
| .00625 | $1.5 \times 10^3$ | $4.2 \times 10^3$ |
| .003125 | $5.2 \times 10^2$ | $3.2 \times 10^2$ |

The 5' phosphorylated (P32) #25 oligodeoxynucleotide, Table I, was ligated to the carrier molecule T-C-G-A-C-C-C-G-G-G. The ligation reaction was composed of the indicated concentrations of the labelled oligodeoxynucleotide, 0.06 M tris-HCl, pH 7.5, 5 mM dithiotrheitol, 0.5 mM ATP, 5 mM MgCl$_2$, 1 uM of 5' phosphorylated carrier oligodeoxynucleotide and 0.6 Weiss units of T4 DNA ligase in 10 ul. The temperature was 19° C. Samples were diluted 1 to 4 with 80% formamide and 2 ul samples were analyzed by electrophoresis on a 12.5% acrylamide, 7 M urea gel at 50° C. after autoradiography to locate the #25 oligodeoxynucleotide and the ladders of ligated oligodeoxynucleotides, the appropriate regions were excised and counted.

TABLE III

LIGATION OF OLIGODEOXYNUCLEOTIDES TO CARRIER OLIGODEOXYNUCLEOTIDE

| Line # | composition | Pre-ligation (cpm) | Ligation (cpm) |
|---|---|---|---|
| 1 | A—T$^{H*}$ (0.4 × 10$^{-7}$M) G$^S$—T* (0.7 × 10$^{-7}$M) | 10577 | 1350 |
| 2 | A—T$^{H*}$ (0.4 × 10$^{-7}$M) | 11632 | 875 |
| 3 | A—T* (0.85 × 10$^{-7}$M) | 57240 | 68813 |

TABLE III-continued

| | LIGATION OF OLIGODEOXYNUCLEOTIDES TO CARRIER OLIGODEOXYNUCLEOTIDE | | |
|---|---|---|---|
| Line # | composition | Pre-ligation (cpm) | Ligation (cpm) |
| 4 | A—T* (0.15 · 10$^{-5}$M) | 6592 | 6769 |

The indicated oligodeoxynucleotides were ligated to the carrier molecule T-C-G-A-C-C-C-G-G-G. The asterisk denotes the oligodeoxynucleotide that was '5-phosphorylated with P32. The sequences of the oligodeoxynucleotide are listed in Table I. The ligation reaction was composed of the indicated oligodeoxynucleotides and 0.06 M tris-HCl, pH 7.5, 5 mM dithiotrheitol, 0.5 mM ATP, 5 mM MgCl$_2$, 1 UM of 5' phosphorylated carrier oligodeoxynucleotide, and 0.15 Weiss units of T4 DNA ligase in 10 ul. The temperature was 19° C. and the time was 60 minutes. An aliquot of the reaction was diluted 1 to 4 with 80% formamide and 2 ul samples were run on a 10% acrylamide, 7 M urea gel at 50° C. The electrophoresis was terminated when the cyano xylene dye had migrated about 7 cms. After autoradiography to locate the oligodeoxynucleotides the appropriate regions of the gel were excised and counted.

TABLE IV

| RELATIVE ASSOCIATION CONSTANTS | | |
|---|---|---|
| Oligomer pair | Association constant | Value relative to K(A.T/T.A) |
| (A—C/T—G) | K(C/G) | 5 ± 2 |
| (A—T$^H$/T—G$^S$) | K(T$^H$/G$^S$) | 1 ± .5 |
| (A—T/T—G) | K(T/G) | 1/(9 ± 3) |
| (A—T$^H$/T—G) | K(T$^H$/G) | 1/(25 ± 5) |
| (A—C/T—G$^S$) | K(C/G$^S$) | 1/30 |
| (A—T$^H$/T—A) | K(T$^H$/A) | 1/40 |
| (A—C/T—A) | K(C/A) | 1/40 |
| (A—T/T—G$^S$) | K(T/G$^S$) | 1/40 |

Legend. The first oligomer in each expression is written 5' to 3', the second 3' to 5'. The "*" indicates that the amount of duplex ligation was within the experimental uncertainty of the amount found in the absence of the complementary oligodeoxynucleotide.

EXAMPLE 3

IN VIVO REPLICATION OF THE BASE PAIR 5-METHYL-2-PYRIMIDINONE/6-THIOGUANINE

A double stranded oligodeoxynucleotide containing the base pair 5-methyl-2-pyrimidinone/6-thioguanine (MPO/6TG) is synthesized. The synthetic double stranded oligodeoxynucleotide has single stranded 5' ends corresponding to a unique restriction enzyme site. The synthetic double stranded oligodeoxynucleotide is inserted, in vitro, into the unique restriction site of a double stranded DNA vector, plasmid or phage, using the T-4 ligase catalyzed reaction. The insertion of the double stranded synthetic oligodeoxynucleotide into the DNA of the vector causes the inactivation of a protein function specified by the base sequence of the DNA of the vector in the region where the insertion takes place. The protean function lost, for example, the enzyme beta-galactosidase, is not essential for the replication of the vector in infected cells. A strain of E. coli which can be transformed by the addition of external DNA is exposed to the vector carrying the synthetic double stranded oligodeoxynucleotide. The strain of E. coli is chosen so that the presence of a replicating vector in a cell can be distinguished from a cell without the vector. In addition, the E. coli strain has the characteristic of allowing the presence or absence of the non-essential protein function to be detected. The transformed cells are grown in the presence of the bases and/or (deoxy)nucleotides of MPO/6TG. After many generations of replication of the cells and their vectors that do not have the non-essential protein function the vector is isolated. The oligodeoxynucleotide present in the vector DNA is then analyzed for the presence of the base pair MPO/6TG.

In general, the M13 phage and plasmid cloning methodology of Messing (pi M13 cloning/dideoxysequencing Instruction Manual, Bethesda Research Laboratories, Gaithersburg, MD, 1986) will be used. Complementary oligodeoxynucleotides with 12 or more residues will be synthesized using the phosphotriester and/or phosphite-triester methods (Gait, M. J. (Ed.), Oligodeoxynucleotide Synthesis, IRL Press, Oxford, 1984). The double stranded oligodeoxynucleotide will have the base pair 5-methyl-2-pyrimidinone/6-thioguanine (MPO6TG). Single stranded regions at each end of the double stranded oligomer will have the Sal I restriction site overhang sequence (5')TCGA so that the double stranded oligomer can be ligated to the Sal I cloning site in the vector.

Next, the replicative form of phage M13mp18 and the plasmid pUC8 (or 18) will be cut with Sal I and the 5' phosphate of the linearized vectors will be removed using alkaline phosphatase.

The standard litigation reaction mixture for a 10 ul volume will use 2 f moles of linear M13mp 18 or pUC8 (or 18) and 10-30 pmoles of the complementary oligodeoxynucleotides. The high concentration of complementary oligomer is necessary because the association constant of the short oligomers is low. The possible incorporation of concatomers in the vector is not a disadvantage.

Transformation with both M13pm18 and pUC8 (or 18) after ligation will use the DH 5 alpha strain of E. coli (Bethesda Research Laboratories) or an equivalent. In the case of the M13mp18 the DH 5 alpha cells will be plated with E. coli strain JM107 (Yarisch-Perron, et al., Gene, 33:103, 1985) since F' strains are required for M13 phage infection.

In the case of M13mp18, in addition to the standard ingredients of the plating medium, the medium will contain the bases and/or (deoxy(nucleotides of MPO and 6TG at concentrations of 0.001 M to 0.0001 M. Colonies from the white plaques will be isolated and purified on a medium with MPO and 6TG. M13pm18 phage will be produced from cells growing in standard medium with MPO and 6TG added. Single strand DNA from the phage will be isolated by the phenol method, (Maniatis, et al., Molecular Cloning, A Laboratory Manual, Cold Spring Harbor, 1982).

When pUC8 or 18 is used, after exposure to the plasmid, cells from the transformation step will be plated on standard medium with additions of ampicillin, 50 ug/ml, and the bases and/or (deoxy)nucleosides of MPO and 6TG at concentrations of 0.001 M to 0.0001 M. White colonies will be purified and the cells grown in the presence of P32 phosphate to label the nucleic acid. Plasmids will be isolated from the cells using standard methods (Maniatis, et al., ibid).

In analyzing the phage DNA and the plasmid DNA the plasmid will be digested with Sal I restriction enzyme and the small oligodeoxynucleotides purified from the larger DNA of pUC8 by acrylamide gel electrophoresis with the location of the bands by radioautography. The small oligodeoxynucleotides will be eluted from the gel and digested with phosphodiesterase (Maniatis, et al., ibid). The digest will be analyzed by HPLC using a strong anoin exchanger (for example Whatman PXS-1025 SAX 4.6×250 mm) with a linear gradient from 0.007 F $KH_2PO_4$, pH 4.0, to 0.5 F KCl, 0.25 F $KH_2PO_4$, pH 4.5. Authentic 5' deoxynucleotides of MPO and 6TG will be run with the digest. The appearance of peaks of P32 that are identical to the peaks of the added nucleotides of MPO and 6TG will demonstrate that the base pair MPO/6TG has been replicated in vivo.

In addition, M13mp18 single stranded DNA will be used as a template with a universal primer for the synthesis of oligodeoxynucleotides. Two reaction mixtures will be used. One will contain, in addition, the 5'triphosphates of the MPO and 6TG deoxynucleotides. If the bases 6TG and/or MPO are present in the cloning site of the phage DNA synthesis will terminate or the rate will be substantially reduced when the polymerase encounters MPO or 6TG base in the template in the reaction mixture with only standard bases, but will continue through the cloning site in the reaction mixture with MPO and 6TG deoxynucleotide 5' triphosphate. One of the standard nucleoside 5' triphosphates will have an alpha P32. An analysis of the oligodeoxynucleotides synthesized in the two reaction mixtures by acrylamide gel electrophoresis will show much larger oligodeoxynucleotides are produced in the mixture with MPO and 6TG 5' triphosphates than in the mixture without them. As a control, a comparison will be made with synthetic complementary oligodeoxynucleotides with guanine/cytosine or adenine/thymine base pairs in place of the MPO/6TG base pairs.

The invention now being fully described, it will be apparent to one of ordinary skill in the art that many changes and modifications can be made without departing from the spirit and scope of the invention.

I claim:

1. A double stranded genetic sequence consisting of deoxyribonucleic acid (DNA), the duplex structure of said double stranded genetic sequence being maintained by base pairs between complementary bases on each of the strands.

wherein at least one of said base pairs is a complementary base pair consisting of a non-naturally-occurring purine derivative and a non-naturally-occurring pyrimidine derivative;

said non-naturally-occurring purine derivative having the formula:

wherein R1 and R2 are hydrogen, sulfur, oxygen, or amino, and X in ring positions 3 and 7 may each be either carbon or nitrogen;

said non-naturally-occurring pyrimidine derivative having the formula:

wherein R3 and R4 are hydrogen, sulfur, oxygen or amino, and R5 is hydrogen, halogen, —$SCH_3$, —OH, hydroxymethyl, alkoxyl, cyano, methylamino, ntiro, or unsubstituted, or halogen non-naturally-occurring hydrocarbon groups 1-3 carbons, and X in ring positions 1,5 and 6 may each be either carbon or nitrogen;

so long as at least one but no more than two of R1–R4 are sulfur, and hydrogen (H) is a substituent on the base complementary to any S-containing base in a position to form a stable base pair;

further wherein said purine derivative and said pyrimidine derivative preferentially form a stable base pair with each other in the presence of the naturally occurring base adenine (A), thymine (T), guanine (G) and cytosine (C), so that structural integrity of said double stranded genetic sequence containing said purine derivative and said pyrimidine derivative is maintained.

2. The genetic sequence of claim 1, further comprising a plurality of said non-naturally-occurring purine derivative and said non-naturally-occurring pyrimidine derivative complementary base pairs.

3. A method for inhibiting growth of a transformed cell whose genetic sequence is the genetic sequence of claim 1, comprising culturing said cell in culture media containing an amount of said non-naturally-occurring purine derivative or said non-naturally-occurring pyrimidine derivative which limits replication of said genetic sequence, wherein said cell cannot synthesize said non-naturally-occurring purine derivative or said non-naturally-occurring pyrimidine derivative.

4. A method for inhibiting growth of a transformed cell whose genetic sequence is the genetic sequence of claim 2, comprising culturing said cell in culture media containing an amount of said non-naturally-occurring purine derivative or said non-naturally-occurring pyrimidine derivative which limits replication of said genetic sequence, wherein said cell cannot synthesize said non-naturally-occurring purine derivative or said non-naturally-occurring pyrimidine derivative.

5. The genetic sequence of claim 2, wherein said non-naturally-occurring purine derivative is 2-thioketo-purine and said non-naturally-occurring pyrimidine derivative is 4-thioketo-pyrimidine.

6. The genetic sequence of claim 2, wherein said non-naturally-occurring purine derivative is 2-keto-purine and said non-naturally-occurring pyrimidine derivative is 2-amino-4-thioketo-pyrimidine.

7. The genetic sequence of claim 2, wherein said non-naturally-occurring purine derivative is 6-thioketo-purine and said non-naturally-occurring pyrimidine derivative is 2-thioketo-pyrimidine.

8. The genetic sequence of claim 2, wherein said non-naturally-occurring purine derivative is 6-keto-purine and said non-naturally-occurring pyrimidine derivative is 2-thioketo-4-amino-pyrimidine.

9. The genetic sequence of claim 2, wherein said non-naturally-occurring purine derivative is 2-aminopurine and said non-naturally-occurring pyrimidine derivative is 2-keto-4-thioketo-pyrimidine.

10. The genetic sequence of claim 2, wherein said non-naturally-occurring purine derivative is purine and said non-naturally-occurring pyrimidine derivative is 2-4-thioketo-pyrimidine.

11. The genetic sequence of claim 2, wherein said non-naturally-occurring purine derivative is 2-amino-6-thioketo-purine and said non-naturally-occurring pyrimidine derivative is 2-keto-pyrimidine.

12. The genetic sequence of claim 2, wherein said non-naturally-occurring purine derivative is 2-keto-purine and said non-naturally-occurring pyrimidine derivative is 4-thioketo-pyrimidine.

13. The genetic sequence of claim 2, wherein said non-naturally-occurring purine derivative is 2-keto-purine and said non-naturally-occurring pyrimidine derivative is 4-thioketo-pyrimidine.

14. The genetic sequence of claim 2, wherein said non-naturally-occurring purine derivative is 2-thioketo-purine and said non-naturally-occurring pyrimidine derivative is 4-keto-pyrimidine.

15. The genetic sequence of claim 2, wherein said non-naturally-occurring purine derivative is 6-thioketo-purine and said non-naturally-occurring pyrimidine derivative is 2-keto-pyrimidine.

16. The genetic sequence of claim 2, wherein said non-naturally-occurring purine derivative is 2-keto-6-thioketo-purine and said non-naturally-occurring pyrimidine derivative is 2-amino-pyrimidine.

17. The genetic sequence of claim 2, wherein said non-naturally-occurring purine derivative is 2-thioketo-6-thioketo-purine and said non-naturally-occurring pyrimidine derivative is pyrimidine.

18. The genetic sequence of claim 2, wherein said non-naturally-occurring purine derivative is 2-thioketo-6-keto-purine and said non-naturally-occurring pyrimidine derivative is 4-amino-pyrimidine.

* * * * *

UNITED STATES PATENT AND TRADEMARK OFFICE
CERTIFICATE OF CORRECTION

PATENT NO. : 5,126,439
DATED : June 30, 1992
INVENTOR(S) : Harry P. Rappaport

It is certified that error appears in the above-identified patent and that said Letters Patent is hereby corrected as shown below:

Column 19, lines 56-63, atoms at positions 3 and 7 of the formula should be changed from "N" to "X".

Column 20, lines 12-13, replace "non-naturally-occurring" with --substituted--.

Signed and Sealed this

Ninth Day of April, 1996

*Attest:*

BRUCE LEHMAN

*Attesting Officer*     *Commissioner of Patents and Trademarks*